US008137335B2

(12) United States Patent
Duirs

(10) Patent No.: US 8,137,335 B2
(45) Date of Patent: Mar. 20, 2012

(54) TREATMENT AND CONTROL DEVICE

(76) Inventor: Graham Francois Duirs, Hamilton (NZ)

( * ) Notice: Subject to any disclaimer, the term of this patent is extended or adjusted under 35 U.S.C. 154(b) by 663 days.

(21) Appl. No.: 10/572,991

(22) PCT Filed: Sep. 23, 2004

(86) PCT No.: PCT/NZ2004/000231
§ 371 (c)(1),
(2), (4) Date: Jan. 10, 2007

(87) PCT Pub. No.: WO2005/027775
PCT Pub. Date: Mar. 31, 2005

(65) Prior Publication Data

US 2007/0239181 A1 Oct. 11, 2007

(30) Foreign Application Priority Data

Sep. 23, 2003 (NZ) ....................................... 528240

(51) Int. Cl.
*A61M 31/00* (2006.01)

(52) U.S. Cl. ..... 604/514; 604/104; 604/264; 119/14.21; 119/14.19

(58) Field of Classification Search .................. 604/514, 604/104, 264; 119/14.21, 14.19
See application file for complete search history.

(56) References Cited

U.S. PATENT DOCUMENTS

| | | | | |
|---|---|---|---|---|
| 1,688,795 | A | 10/1928 | Aas | |
| 1,797,339 | A | 3/1931 | Gudmand-Hoyer | |
| 1,899,492 | A | 2/1933 | Beebe | |
| 1,957,673 | A | 5/1934 | Sayre | |
| 1,995,051 | A | 3/1935 | Benson | |
| 2,244,027 | A * | 6/1941 | Smith | 604/287 |
| 2,368,576 | A | 1/1945 | Smith | |
| 2,498,374 | A * | 2/1950 | Martin | 604/514 |
| 2,832,343 | A | 4/1958 | Mose | |
| 3,030,960 | A | 4/1962 | Turner | |
| 3,703,898 | A | 11/1972 | Zackheim | |
| 3,821,956 | A | 7/1974 | Gordhamer | |
| 3,938,517 | A | 2/1976 | Anderson | |
| 4,331,651 | A * | 5/1982 | Reul et al. | 424/434 |
| 4,385,633 | A * | 5/1983 | Child | 604/246 |
| 6,221,060 | B1 * | 4/2001 | Willard | 604/264 |
| 6,756,048 | B1 * | 6/2004 | Sano et al. | 424/426 |

FOREIGN PATENT DOCUMENTS

EP 1031327 A2 8/2000

* cited by examiner

*Primary Examiner* — Bhisma Mehta
*Assistant Examiner* — Edelmira Bosques
(74) *Attorney, Agent, or Firm* — Knobbe Martens Olson & Bear LLP

(57) ABSTRACT

A treatment or controlling device that is capable of being inserted into a teat orifice. The device is also capable of being held in position in the teat streak canal once it is inserted in a teat orifice. The device is configured to act as a substrate for natural keratin deposition.

11 Claims, 4 Drawing Sheets

TREATMENT AND CONTROL DEVICE

RELATED APPLICATIONS

This application is U.S. National Phase of International Application PCT/NZ2004/000231, filed Sep. 23, 2004 designating the U.S., and published in English as WO 2005/027775 on Mar. 31, 2005, which claims priority to New Zealand Patent Application No. 528240, filed Sep. 23, 2003.

TECHNICAL FIELD

This invention relates to a treatment and control device.

Reference throughout the specification now shall be made to use of the device in relation to teats and mammary glands.

BACKGROUND OF THE INVENTION

Infection in the udder is a major problem in dairy cows. It is caused by bacteria which in most cases enters the udder through the teat orifice.

It is the teat orifice or the streak canal that forms a primary defense mechanism to invading micro-organisms. Deposits of keratin sit in the streak canal (sometimes known as the teat end canal) to form a natural defensive plug. Keratin contains high levels of naturally occurring antibacterial substances which inhibit the passage of bacteria. The keratin deposits are more dense in dry cows than lactating cows. The reason for this is that during the dry period, keratin forms a solid plug which protects the teat from invading bacteria.

Sometimes dry period sub clinical mastitis infections will occur and these can be carried on to manifest themselves as clinical mastitis at calving or during the next lactation. *Streptococcus uberis* is a type of bacteria that commonly infects dry udders and appears as clinical mastitis at calving time.

Some types of treatments are administered at drying off to cure sub-clinical infections or as a preventative treatment designed to protect the udder from new infections during the high-risk dry period, especially immediately after drying off. Dry period therapy often consists of antibiotics which are in a sustained release base to provide prolonged antibacterial protection during the early dry period when the streak canal keratin is forming a natural seal or barrier against such infection risks.

Once the streak canal seal is in place, the risk of infections is lower. However, there is a tendency for new infections to occur during the immediate post-drying off period if cows are not treated with a protective dry period antibiotic. This is more likely to occur when teat end damage or trauma has occurred that can delay or disrupt the formation of the streak canal seal.

Additionally, the build up of milk pressure immediately following the cessation of regular milking at drying off may cause milk to leak from the teats, disrupting keratin formation and increasing the risk of infection.

Treatments for dry period therapy are often administered as infusions of antibiotics by a plastic needle or nozzle placed into the teat orifice and into the streak canal or teat cistern (papillary sinus).

One example of this is U.S. Pat. No. 4,472,374 which discloses an intramammary composition containing a siloxane elastomer incorporating an antibacterial agent.

In order to facilitate application to the teat, U.S. Pat. No. 4,472,374 requires that "the elastomer must be of sufficiently low viscosity to facilitate the application to the mammary glands by injection via the streak canal and teat cistern". U.S. Pat. No. 4,472,374 further teaches that the elastomer must remain sufficiently elastic to remain in place and soft enough to be milked-out at the onset of lactation. As such, an inert fluid silicone may be used to obtain "a liquid elastomer of the desired properties".

Best results were obtained in U.S. Pat. No. 4,472,374 when the majority of the elastomer was infused into the teat sinus, and the remainder of the elastomer was discharged into the streak canal as the infusion means/applicator was withdrawn out of the teat.

U.S. Pat. No. 4,472,374 however suffers from a number of disadvantages. In order for the low viscosity composition to be retained within the udder during the dry period, the majority of the compositions must be infused into the teat sinus, where the antibacterial agents are diluted and of less use in preventing mastitis and may also cause additional problems such as irritations and residues.

The low viscosity composition of U.S. Pat. No. 4,472,374 also has no defined form, and thus does not permit any control to be exercised over the placement, size or shape of the elastomer infused into the streak canal. Accordingly, it is not possible for a user to control the placement or volume of elastomer infused into the streak canal and thus it is also not possible to control the dose of antibacterial agent delivered.

Further, due to the low viscosity of the composition, it is difficult to ensure complete removal before lactation commences.

Lactating animals used for milk production are exposed to mechanical milking machines, normally twice a day. These machines apply vacuum pulsation to the teat for milking purposes.

Understandably, mechanical milking can cause damage to the teat end. High vacuum, faulty pulsation and over-milking can bruise tissue and erode the teat end—breaking down the natural defenses of the teat. This can occur from infected teat lesions forming, damaged tissue and a loss of teat end integrity allowing bacteria to enter the udder. These will also influence dry period new infections with the inability of the teat to form an effective keratin shield over the dry period.

In some situations, surgical procedures may be used to repair damaged teats. After surgery, an intramammary antibiotic is infused into the teat cistern to prevent and/or treat mastitis, before a teat insert or sterile silicone implant is inserted into the teat canal to prevent the narrowing or collapse of the teat canal after surgery. However, these inserts are designed to provide temporary support for the teat canal of damaged teats only and do not themselves contain any medicament.

Mastitis occurs in various forms depending on the type of micro-organism causing the infection. It causes lost milk production, and adversely affects the flow and quality of milk. During lactation, mastitis can occur as clinical mastitis, which is visually recognising and treatable. Clinical mastitis is treated during lactation using a multiple number of antibiotic infusions at milking time. Care must be taken to avoid contaminating the milk supply with antibiotic residues.

The economic significance of mastitis is considerable. The common way to treat mastitis is with intramammary antibiotics infused into the udder through the teat orifice and via the streak canal. The antibiotic is absorbed into the alveolus in secretary tissue where the infection normally resides. These antibiotics come in various formulations but usually consist of an antibiotic formulated in paste or oil base which is infused by inserting a plastic tip through the orifice and squeezing the antibiotic from the tube into the udder.

The antibiotic is infused after milking. Since the cow must be milked regularly to maintain lactation and also to avoid discomfort, the cow is milked at the next milking period, removing much of the antibiotic treatment. Consequently, repeated treatments are infused to maintain adequate drug levels. This milk must be discarded as it is contaminated with inhibitory substances.

Other problems associated with the present treatment of mastitis include:

Treatment of cows at drying off as a preventative procedure requires an antibiotic which can remain in the udder for 20 days over the cow's dry period. The antibiotic must have an active duration which does not contaminate the milk of fresh calved cows with antibiotic residues in the immediate post-calving period. In particular, antibacterial activity is important over the first ten days of drying off.

Treatment of clinical mastitis during lactation requires the infusion of one to three successive antibiotics into a lactating udder. Consequently, the cow must be milked each day with the treatment period being up to three days. Therefore when the antibiotic is infused, the main bulk of the antibiotic is removed from the udder when the cow is milked at the next milking, requiring a further treatment after the milking to restore the required level of antibiotic to treat the infection.

The wastage of antibiotic in the removed milk and constant administration of a further treatment is costly. There is also potential risk from the farmer inadvertently allowing the milk to go to the bulk tank. This can lead to the farmer incurring severe antibiotic residue penalties.

All references, including any patents or patent applications cited in this specification are hereby incorporated by reference. No admission is made that any reference constitutes prior art. The discussion of the references states what their authors assert, and the applicants reserve the right to challenge the accuracy and pertinency of the cited documents. It will be clearly understood that, although a number of prior art publications are referred to herein, this reference does not constitute an admission that any of the documents form part of the common general knowledge in the art, in New Zealand or in any other country.

It is acknowledged that the term 'comprise' may, under varying jurisdictions, be attributed with either an exclusive or an inclusive meaning. For the purpose of this specification, and unless otherwise noted, the term 'comprise' shall have an inclusive meaning—ie that it will be taken to mean an inclusion of not only the listed components it directly references, but also other non-specified components or elements. This rationale will also be used when the term 'comprised' or 'comprising' is used in relation to one or more steps in a method or process.

It is an object of the present invention to address the foregoing problems or at least to provide the public with a useful choice.

Further aspects and advantages of the present invention will now be described by way of example only.

SUMMARY OF THE INVENTION

According to one aspect of the present invention there is provided a treatment or controlling device capable of insertion into a teat orifice, and the device also capable of being held in position in the teat streak canal once inserted therein characterised in that the device is configured to act as a substrate for natural keratin deposition.

According to another aspect of the present invention there is provided a treatment or controlling device substantially as described above characterised in that the device is configured to deliver one or more treatment substances to the streak canal.

In preferred embodiments of the present invention the device shall be used in relation to bovine teats. However, it is anticipated the present invention may find use in relation to a number of animal species used for milk production, having high yielding mammary glands and a plurality of teats each consisting of teat cistern, streak canal and a single teat end orifice.

It should be understood that the term "streak canal" relates to the canal located between the papillary sinus and the teat end orifice. The streak canal is also known as the teat end canal and these terms may be used interchangeably.

The streak canal is thus distinguished from the teat cistern, which is also known as the papillary sinus or teat sinus.

In preferred embodiments the device is designed to deliver one or more treatment substances for a period equivalent to the period it takes endogenous keratin plugs to form, thereby providing early protection from infections before the natural defence system of the teat has been activated.

In situations where the formation of endogenous keratin plugs may be impaired, the device may be configured to degrade over time and integrate with endogenous keratin to form a composite plug.

In preferred embodiments the device is configured to prevent the unwanted passage of substances through the streak canal.

In preferred embodiments the device will act to shield and protect the udder from bacterial infection that normally enters the teat cistern via passage through the streak canal, and then invades the lactiferous sinus or udder due to failure of the teat's natural defences. However, those skilled in the art should appreciate the device may be used for a number of other applications, Including but not limited to alleviating the build up of milk pressure at drying off immediately following the cessation of regular milking, whilst providing treatment substances to prevent infection; acting as a physical barrier to prevent milk leaking from damaged or abnormal teats; and/or to seal the teat following a form of therapeutic treatment.

In preferred embodiments of the present invention the device is made of a preformed matrix such as silicone which is able to deliver treatment substances, in specific quantities at the specific designated site. In contrast, the low viscosity pastes and gels previously used were not able to provide precise positioning of substance or control over the volume of composition infused, or thus the amount of antibacterial agent delivered.

Further, the low viscosity compositions were also difficult to remove following treatment, increasing the risk of residues contaminating the milk supply or blocking milk filters.

In preferred embodiments of the present invention, the delivery of the treatment substances is by a diffusion of those substances from the matrix that the device is made from.

In other preferred embodiments the treatment substance may be delivered through dissolution processes of the device matrix or by the placement of appropriate treatment substances within the inner core of the device under various delivery systems.

For example, the device may be made of a matrix which is impregnated with appropriate treatment and/or barrier substances. For example, these substances may include antibiotics, antibacterial substances, tissue growth enhancers, vitamins and minerals, hormones, oxytocin, prolactin and healants.

Additionally, the treatment substances may be used to improve the healing of damaged teats.

In other embodiments the device may simply act as a plug to form a physical barrier.

The passage of harmful micro-organisms may thus be prevented by the sustained delivery of small, localised doses of such treatment substances in the streak canal and at the teat orifice—negating the requirement for high level infusions of traditional antibiotic compositions to prevent or treat infections.

A considerable advantage of the present invention is that its solid form allows the substances to be applied to the streak canal where they are needed, rather than into the teat cistern where substances are of little use or may cause additional problems such as irritation.

This localised, low volume application in the part of the teat exposed to the external environment ensures that bacteria can be killed at the point of entry, thus only a low amount of treatment substance is required, being not only good for the animal but also less expensive.

Further, as the treatment is not applied to the internal milk secretory glands, there is less risk of contamination of the milk by treatment residues. In contrast, previous methods such as those disclosed by U.S. Pat. No. 4,472,374 deliver high levels of treatment substances into the internal teat cistern and as such care is required to ensure all residues are removed to avoid contaminating the milk supply.

The shape and design of the device is preferably such that it can Withstand the build up of milk pressure that occurs at drying off immediately following the cessation of regular milking in the period before udder involution, without the device being ejected from the teat.

In preferred embodiments the device has a conduit to alleviate the build up of milk pressure at drying off. The conduit may have a one-way valve or other such mechanism to prevent a bacterial infection entering the teat via the conduit. Alternatively, the delivery of one or more treatment substances may be used to protect the teat from infection.

Immediately prior to calving, the udder of the cows become engorged at the onset of lactogenesis. The device can then be ejected either naturally, from calf suckling, or from hand stripping.

Preferably, the configuration and material construction of the present invention is such that the pressure generated as a consequence of lactogenesis is sufficient to dislodge the device from the streak canal. This is desirable so that once the cow has calved, the calf can immediately suckle on the teat unimpeded. This can understandably save the farmer a considerable amount of labour.

In the event that a device should fall into the teat cistern the design is preferably such that the device can be ejected by using the force of hand stripped milking as a means of removing the device, or alternatively will degrade quickly.

The applicant in preferred embodiments of the present invention has designed the device so that it can enhance the role of keratin as a primary defense. The applicant envisaged that a device in accordance with preferred embodiments will act as a symbiotic interface with endogenous keratin such that the accumulative beneficial effect of both defense systems (that is the diffusion of external treatment substances and the keratin) are greater than the keratin alone.

The shaft of the device may come in a variety of forms and in one embodiment may be completely smooth so as to avoid irritating the streak canal. However, in preferred embodiments the shaft has a number of grooves along its length. There may of course be other recesses in the device, for example a spiral thread.

Having a spiral thread would allow the device to be rotated into the teat in a manner less likely to disrupt any keratin contained in the streak canal. It is anticipated the helical shape will also allow the device to better integrate with keratin in the streak canal through deposition of keratin in the helical grooves.

In some embodiments there may also be a plurality of protrusions spaced along the length of the shaft. These protrusions can be tapered or rounded to allow easy insertion of the device while making it more difficult for the device to be dislodged during normal movement of the animal.

The grooves and protrusions may be manufactured in such a way to cause minimal dislodgment of keratin at insertion and to contain endogenous keratin as well as to sustain the synthesis of the keratin, so not to impair the teat's natural defenses.

The applicant believes that the provision of grooves and protrusions will accommodate the keratin produced by the teat which contains natural antibacterial substances enabling the symbiosis between the natural defense system and the provided defense system.

It should be appreciated that the nature of the device itself in many respects acts as a physical equivalent of natural keratin such that both the physical barrier and inhibitory components of natural keratin are enhanced.

The device also preferably acts as an immediate plug over the immediate post drying off period before natural keratin plugs have formed, to control any infections that may be resident in the end canal and prevent new mastitic infections over the post drying off period.

Preferably the device is made of a soft, non-irritant biomedical substance (although it can be made of other substances). Preferably the device is sufficiently pliable so that the streak canal walls compress the device in a similar manner that the walls normally compress keratin deposits. Thus, the streak canal walls can act in holding in the device in a natural position within the streak canal.

Preferably the device is of a dimension that can be readily inserted into the teat orifice with an acceptable degree of stretching of the streak canal wall.

Further, the device is preferably designed to enable it to sit and be retained within the streak canal structure such that the teat end is able to close naturally and the surrounding smooth muscle layer can form naturally and without irritation around the body of the device. In this manner the device can be held firmly in place, avoiding loss by movement of the device and be retained without interfering with normal keratin deposition.

In preferred embodiments of the present invention the shape and design of the device are such that it will fit entirely within the streak canal, having no protrusions into the teat cistern, being defined as penetrating inwards beyond the Furstenburg's rosette complex; or penetrating outwards beyond the external epithelium at the orifice of the teat end that may act as a vector for foreign material to enter the teat and cause infection.

It is also anticipated that by avoiding any external protrusions from the teat end and allows sufficient space between the device and teat orifice, keratin can fill the orifice and form a plug normally.

The combination of the device and the naturally occurring keratin aims to increase the teat's natural defences against infection to a greater degree than keratin alone, particularly when teat ends may be damaged or eroded from milking machine trauma.

In some other embodiments there may be additional structural features on the device, which enhance its retention within the streak canal. For example, the device may include a bulb or some other projection which does not irritate the teat tissues but provides sufficient resistance to removal from the teat during everyday activity by the cow. However, the design must be such that the device can be removed by the presence of milk build up as lactogensis commences or be removed by a farmer or veterinarian.

It is envisaged that the bulb in addition to its role of locating the teat plug and preventing fall-out will also provide a cushion for the terminal end of an applicator if one is used to insert the device.

The retaining device will now be referred to as a bulb, although this description should not be seen as limiting. It is envisaged that the bulb is connected to a shaft which fits within the streak canal. In some embodiments, the shaft may be of a length comparable to an average streak canal such that the bulb sits inside the teat cistern, in such a way as to not irritate or disturb tissue.

In some embodiments the device may include a teat cap. The teat cap may have a number of functions.

One function may be merely to prevent the device penetrating too far into the teat, therefore the teat cap acts as a stop.

Another function is to act as a barrier to protect the teat end and streak canal and to enhance the animal's own primary teat defence mechanism against new infections entering the udder through the teat end.

Preferably, the teat cap is designed to enhance retention of the device. The teat cap may also be configured to dislodge from the teat after a certain period of time, once the streak canal has been sealed. In such embodiments, epithelial adhesives may be used to releasably attach the teat cap to the teat.

In preferred embodiments the present invention will also act as a viable plug or shield in the streak canal in situations where the teat end has suffered damage or trauma from milking machines (teat end erosion) disease or injury, or situations where a naturally occurring effective keratin plug is unable to form, which previously rendered the teat susceptible to new infections.

The device may also act as a plug to prevent the leakage of milk from the udder between milking and lactating cows naturally susceptible to this condition or from teat end damage.

In some embodiments, the device may have a recess which extends at least part of the axial length of the device and as a reservoir to hold one or more treatment substances.

In some embodiments of the present invention the recess may extend substantially the axial length of the device to form a conduit.

For example, it is desirable to deliver into the udder treatment substances as previously defined. Thus in the present invention, these substances may be injected through the conduit and out the distal end of the device into the teat cistern.

In other embodiments the substances may pass outwards through the walls of the shaft into the streak canal.

The conduit may also allow the passage of instruments, applicators or other devices.

In other preferred embodiments the conduit may provide a mechanism through which the build up of milk pressure that occurs at drying off immediately following the cessation of regular milking can be alleviated.

In other embodiments the device may act as an implant for the purposes of future delivery of substances to the lactiferous sinus, and may remain in position for an extended period of time.

In other embodiments, there may be provided an alternative delivery device which can utilise the present invention. For example, there may be provided a mechanism which can be anchored to the streak canal device for later retrieval after the treatment period.

Such a mechanism may be a collapsible slow release membrane balloon. The balloon can be inserted through the device when in collapsed form. The balloon can then be injected or infused via the device with treatment substances. Once the substances have been delivered to the teat, the balloon can then be withdrawn in its collapsed form through the device.

The balloon may deliver the substances through for example, dissolution and therefore will collapse naturally. In other embodiments, the balloon may be punctured to collapse it before it is withdrawn through the streak canal device.

To enable accurate placement of the collapsible balloon within the teat cistern, the device may act as an anchor for the balloon component of the device.

It should be appreciated that the provision of an aperture in the device may in some instances allow the cows to be milked while the device is in position to control the teat orifice dilation and/or closure to control and/or improve milk harvesting.

For example, the device may have a two-way valve system so that milk can be removed from the udder and the cow milked with the device in place, yet still allowing substances to be inserted through an alternate valve as described above.

This may be achieved by the flexibility of the material used for the device and the configuration of the valves (for example, flap valves) within the apertures.

A single aperture device may also be milked to open and close as a normal teat being milked.

In other embodiments of the present invention there may be provided a controlled aperture or port within the device. This may be mechanical or electronic. As discussed previously, considerable damage can be suffered by the teats during the milking process as a consequence of the vacuum pulsation used. This invention provides aperture control for the enhancement of milk harvesting.

For example, electronics within the device may open or close the aperture as required by a milking machine.

Again, for example, instead of vacuum pulsation, there may be provided an inductive pulse which causes a solenoid or magnet to open and close the orifice as desired. Other methods of control are also envisaged.

According to a further aspect of the present invention there is provided a method of treating an animal characterised by the step of inserting a device substantially as described above in the animal's teat orifice.

According to another aspect there is provided a method of treating an animal using a treatment or controlling device, characterised by the step of inserting said device into a teat orifice during involution, the device capable of being held in position in the teat streak canal once inserted therein and wherein the device acts as a substrate for natural keratin deposition.

In preferred embodiments the method further includes the step of delivering one or more treatment substances to the streak canal.

BRIEF DESCRIPTION OF DRAWINGS

Further aspects of the present invention will become apparent from the following description which is given by way of example only and with reference to the accompanying drawings in which.

DETAILED DESCRIPTION OF THE PREFERRED EMBODIMENT

Figure 1:
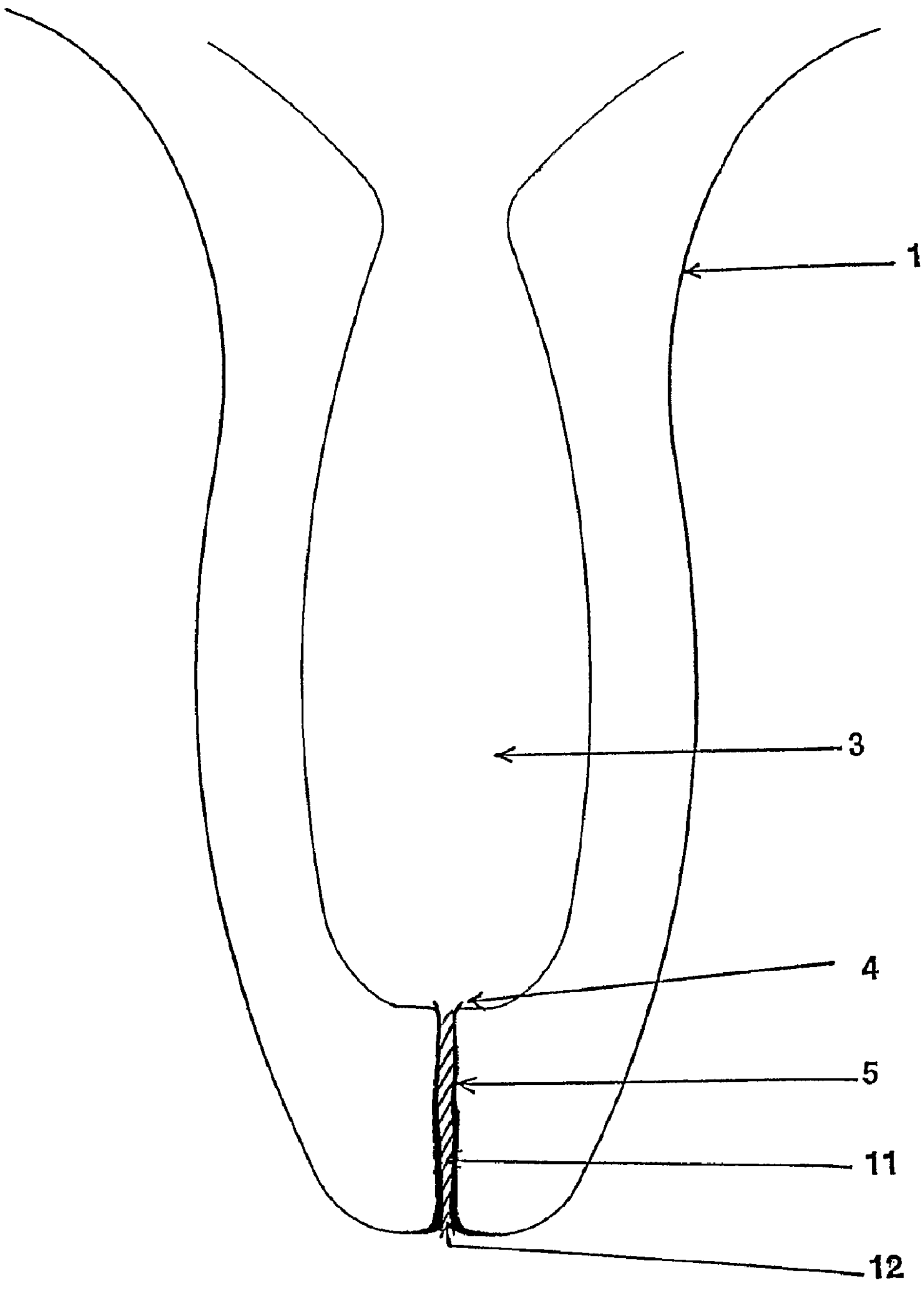
FIG. 1 is a diagram showing the anatomy of a bovine teat.

FIG. 1 illustrates the anatomy of a bovine teat (1) so as to provide some clarification in terms of the placement of the present invention and its interaction with the anatomy of the teat (1). It should be noted that the streak canal (sometimes known as the teat end canal) (5) is at the entrance (12) to the teat. The teat cistern (papillary sinus) (3) is the volume that the streak canal (5) opens into.

Figure 2:
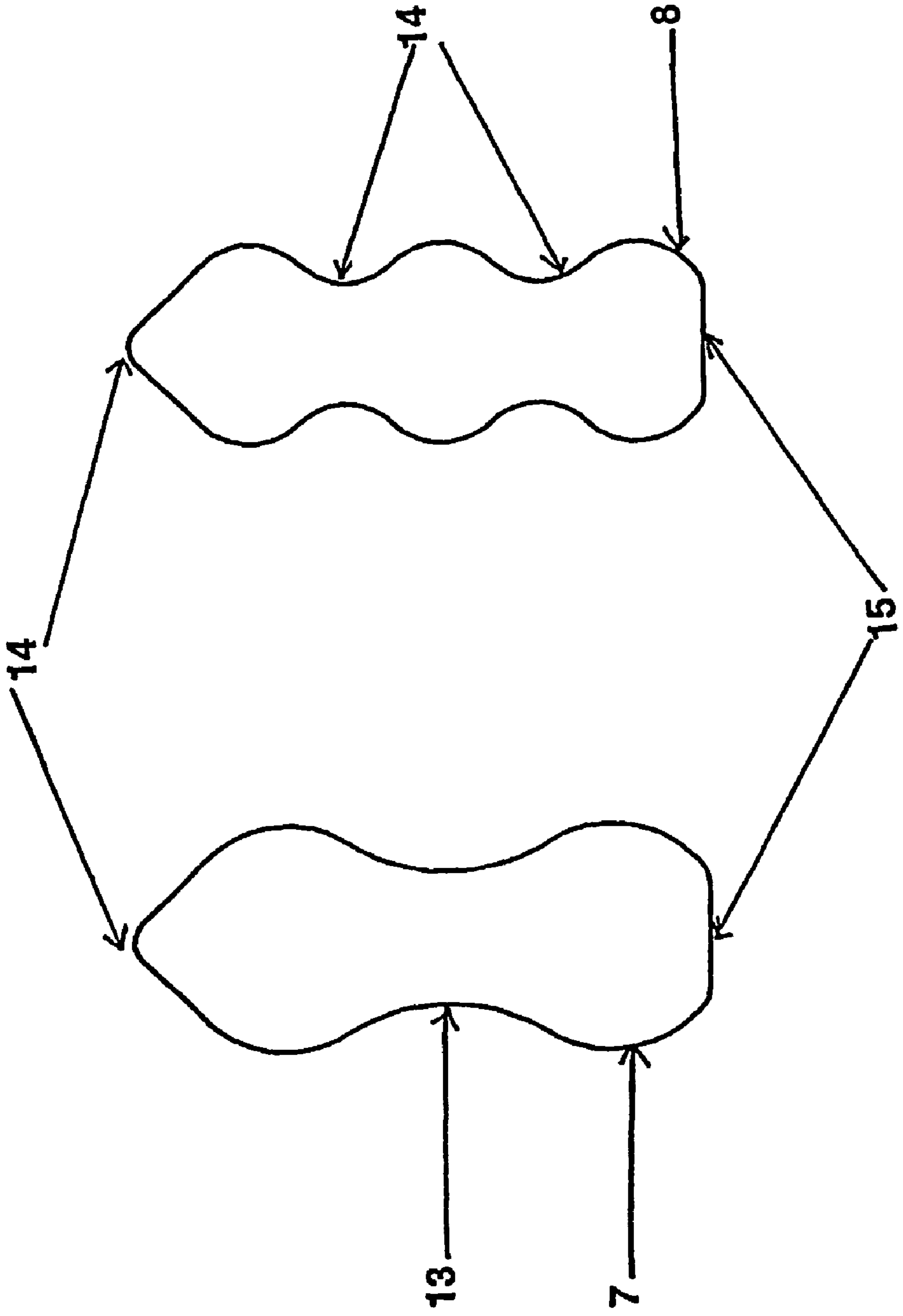
FIG. 2 is a perspective view of two embodiments of the present invention.
Figure 3:
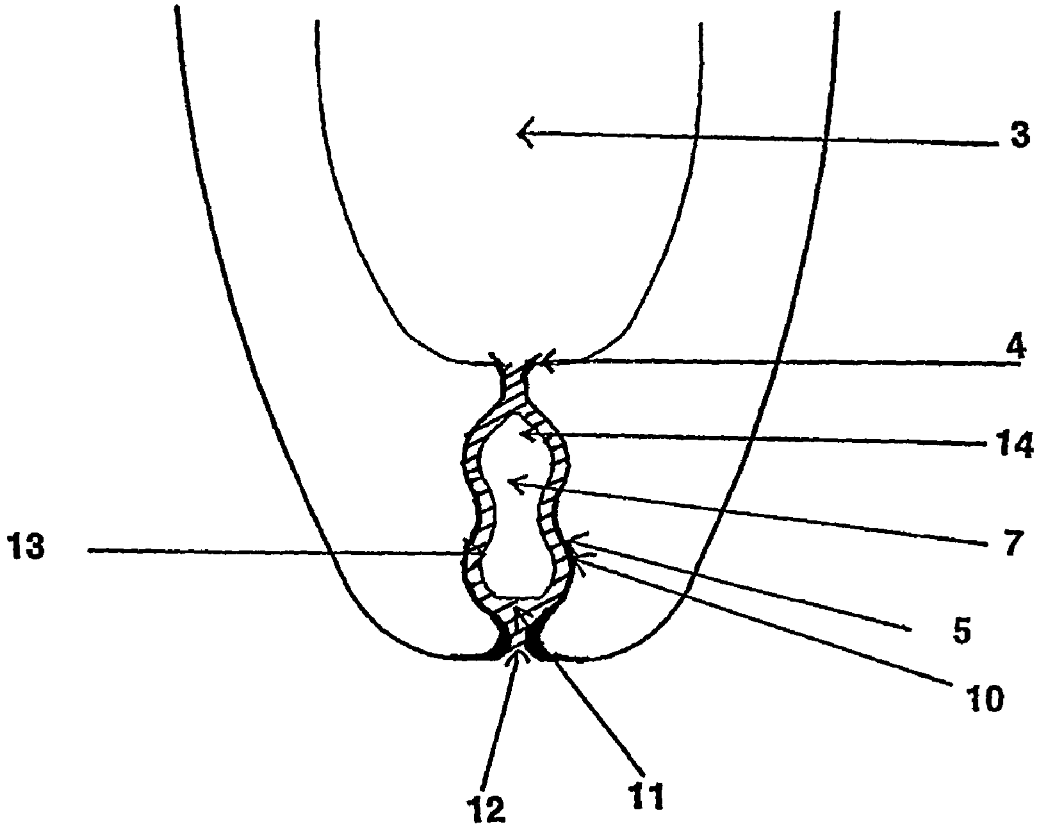
FIG. 3 is a cross-sectional view of one embodiment illustrated in FIG. 2, in position in a bovine teat.

With respect to FIGS. 2 and 3, there is illustrated a streak canal device (7, 8) in accordance with two embodiments of the present invention.

The device (7, 8) is made of a solid, pliable preformed matrix which can be easily inserted and removed, but can be retained during the normal movement of the animal.

The device (7, 8) has a pointed proximal end (14) to facilitate insertion, and a blunt distal end (15) to provide a location for an applicator for insertion.

The device (7, 8) also includes a number of indented surfaces (13, 14) which act to capture and retain natural keratin (11) being produced by the streak canal (5). The keratin is a natural antibacterial substance which assists in improving the well-being of the teat (1).

The shape of the device (7, 8) allows the surrounding smooth muscle layer (10) of the streak canal (5) to form naturally and without irritation around the body of the device (7, 8), such that the device (7, 8) is held firmly in place, avoiding loss of movement of the device (7, 8) and be retained without interfering with normal keratin (11) deposition.

The length of the device (7, 8) is configured such that the device (7, 8) is located entirely within the streak canal, enabling the teat end to seal with keratin naturally (11).

The device (7, 8) is shaped so as to not have any sharp edges that could irritate the delicate tissues of the teat. The device (7, 8) has sufficient width that it can be eased into the streak canal (5) and sit near the Furstenburg's Rossette (4) at the top of the streak canal (5). This helps to retain the device (7, 8) within the streak canal (5).

Figure 4:
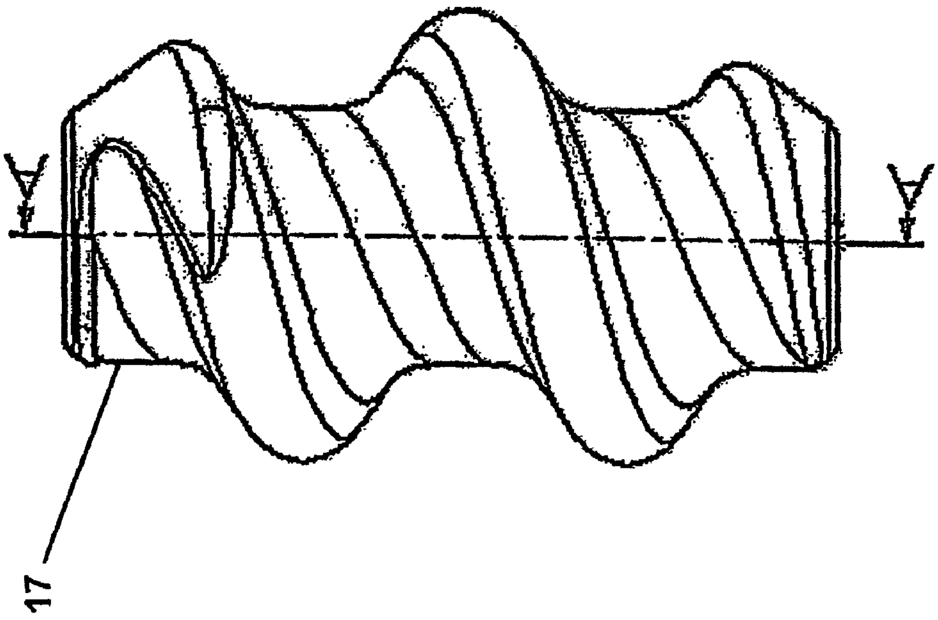
FIG. 4 is a perspective view of another embodiment of the present invention.

FIG. 4 illustrates a device (17) in the form of a helical spiral thread.

The device (17) allows the device (17) to be rotated into the teat in a manner less likely to disrupt any keratin contained in the streak canal.

The helical shape is also designed to better integrate with endogenous keratin in the streak canal by deposition of keratin within the helical groove.

Figure 5:
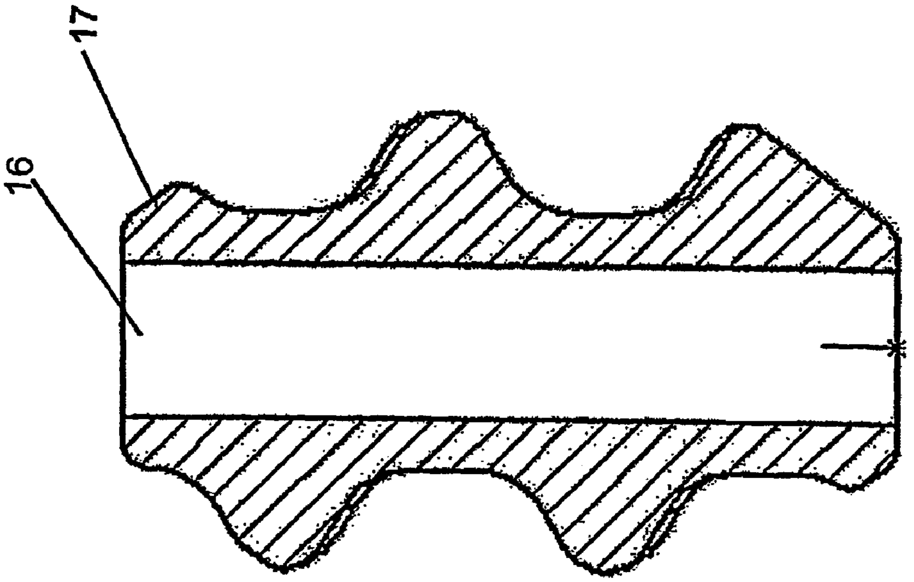
FIG. 5 is a cross-sectional view along line A-A of the device in FIG. 4.

FIG. 5 illustrates a device (17) includes a conduit (16) extending the axial length of the device (17) to permit the passage of instruments and/or substances through the device, and to provide a means of inserting the device (17) into the teat.

In some embodiments the conduit (16) is configured to alleviate the build up of milk pressure that occurs at drying off immediately following the cessation of regular milking.

With respect to FIG. 6, there is illustrated a device (21) in accordance with one embodiment of the present invention.

The device (21) includes a teat cap (22) attached to the shaft (23) of the device (21). At the end of the shaft (23) is a bulb (24).

The cap (22) covers the end of the teat protecting the teat end from further damage and also acting as a stop by preventing the device (21) from being pushed too far into the teat. The teat cap (22) has a conduit in its centre (not shown).

The shaft (23) has a number of grooves (26) which act to capture and retain natural keratin being produced by the teat canal.

The centre of the shaft (23) is hollow with a conduit (not shown) which can have injected into (or contain) one or more treatment substances. These substances may in some embodiments dissolve through the walls of the shaft (23) into the teat canal. In other embodiments, the one or more treatment substances may be injected through and out an aperture (not shown) in the bulb (24).

The bulb (24) is shaped so as to not have any sharp edges that could irritate the delicate tissues of the teat. The bulb (24) has sufficient width that it can be eased through the teat canal and sit near the Furstenburg's Rossette at the bottom of the teat cistern. This helps to retain the plug within the teat canal.

Aspects of the present invention have been described by way of example only and it should be appreciated that modifications and additions may be made thereto without departing from the scope thereof as defined in the appended claims.

What we claim is:

1. A method of reducing the chances of infection in an animal's udder following cessation of regular milking or during involution comprising:

inserting a device into an orifice of a teat of the udder and into a teat streak canal following cessation of regular milking or during involution, drying off the animal after the inserting; and retaining the device within the teat streak canal after a build up in milk pressure that occurs immediately after the drying off without the device being ejected;

wherein the device is held in position within the teat streak canal without any part of the device extending outwards beyond an epithelium of the teat orifice, such that the device provides a barrier to passage of infectious agents and particulate matter into the udder.

2. A method of treating an animal as claimed in claim 1 including a further step of delivering one or more treatment substances to the teat streak canal.

3. The method as claimed in claim 1, wherein the retaining comprises retaining the device within the teat streak canal for a time sufficient for the device to integrate with endogenous keratin to form a composite plug.

4. The method as claimed in claim 1, further comprising degrading the device within the teat streak canal over time.

5. The method as claimed in claim 1, wherein the retaining is enhanced by one or more surface features of the device.

6. The method as claimed in claim 5, wherein said one or more surface features include one or more grooves.

7. The method as claimed in claim 5, wherein said one or more surface features include a spiral thread.

8. The method as claimed in claim 5, wherein said one or more surface features include a plurality of protrusions.

9. The method as claimed in claim 5, wherein the inserting of the device occurs with minimal dislodgement of keratin.

10. The method as claimed in claim 1, wherein the device does not extend into a teat cistern.

11. A method of reducing the chances of infection in an animal's udder following cessation of regular milking or during involution comprising:

inserting a device into an orifice of a teat of the udder and into a teat streak canal following cessation of regular milking or during involution, wherein the device is held in position within the teat streak canal without any part of the device extending outwards beyond an epithelium of the teat orifice, such that the device provides a barrier to passage of infectious agents and particulate matter into the udder; and dislodging the device from the teat streak canal by milk pressure generated as a consequence of lactogenesis.

* * * * *